United States Patent
Herbst-Kralovetz et al.

(10) Patent No.: US 9,585,954 B2
(45) Date of Patent: Mar. 7, 2017

(54) MUCOSAL IMMUNIZATION (71) Applicants: Melissa Herbst-Kralovetz, Phoenix, AZ (US); Charles J. Arntzen, Gold Canyon, AZ (US); Daniel Tusé, Sacramento, CA (US)

(72) Inventors: Melissa Herbst-Kralovetz, Phoenix, AZ (US); Charles J. Arntzen, Gold Canyon, AZ (US); Daniel Tusé, Sacramento, CA (US)

(73) Assignee: ARIZONA BOARD OF REGENTS FOR AND ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 8 days.

(21) Appl. No.: 14/068,808

(22) Filed: Oct. 31, 2013

(65) Prior Publication Data
US 2014/0065185 A1 Mar. 6, 2014

Related U.S. Application Data (62) Division of application No. 13/255,427, filed as application No. PCT/US2010/028820 on Mar. 26, 2010, now abandoned.

(60) Provisional application No. 61/164,281, filed on Mar. 27, 2009.

(51) Int. Cl.
| | |
|---|---|
| A61K 39/12 | (2006.01) |
| A61K 39/00 | (2006.01) |
| A61K 39/125 | (2006.01) |
| A61K 39/145 | (2006.01) |
| A61K 39/29 | (2006.01) |
| A61K 39/39 | (2006.01) |

(52) U.S. Cl.
CPC .............. *A61K 39/39* (2013.01); *A61K 39/12* (2013.01); *A61K 39/125* (2013.01); *A61K 2039/5258* (2013.01); *A61K 2039/543* (2013.01); *A61K 2039/5555* (2013.01); *C12N 2770/16034* (2013.01)

(58) Field of Classification Search
CPC ........ A61K 2039/543; A61K 2039/552; A61K 2039/55516; A61K 2039/55561; A61K 2039/55572
USPC ........................................................ 424/184
See application file for complete search history.

(56) References Cited

U.S. PATENT DOCUMENTS

2005/0123550 A1* 6/2005 Laurent et al. ............ 424/184.1
2008/0299152 A1* 12/2008 Richardson et al. ...... 424/216.1

FOREIGN PATENT DOCUMENTS

| WO | WO2005016321 | * | 2/2005 |
| WO | WO2005099752 | * | 10/2005 |
| WO | WO2008094197 | | 8/2008 |
| WO | WO2009039229 | | 3/2009 |
| WO | WO2009103093 | * | 9/2009 |

OTHER PUBLICATIONS

Estes et al., "Noroviruses everywhere: has something changed?", 2006, Gastrointestinal Infections,19:467-474.*
Truong et al. Differentially expressed genes in HIV-1-infected macrophages following treatment with the virus-suppressive immunomodulator murabutide. Virus Res 2004;99:25-33.
De La Tribonniere X et al. A phase I study of a six-week cycle of immunotherapy with Murabutide in HIV-1 patients naive to antiretrovirals. Med Sci Monit 2003;9:PI43-50.
Bahr et al. Clinical and immunological effects of a 6 week immunotherapy cycle with murabutide in HIV-1 patients with unsuccessful long-term antiretroviral treatment. J Antimicrob Chemother 2003;51:1377-1388.
Bahr. Non-specific immunotherapy of HIV-1 infection: potential use of the synthetic immunodulator murabutide. J Antimicrob Chemother 2003;51:5-8.
Amiel et al. Clinical tolerance and immunologic effects after single or repeated administrations of the synthetic immunomodulator murabutide in HIV-1-infected patients. J Acquir Immune Defic Syndr 2002;30:294-305.
Goasduff et al. The transcriptional response of human macrophages to murabutide reflects a spectrum of biological effects for the synthetic immunomodulator. Clin Exp Immunol 2002;128:474-482.
Darcissac et al. Clinical tolerance and profile of cytokine induction in healthy volunteers following the simultaneous administration of ifn-alpha and the synthetic immunomodulator murabutide. J Interferon Cytokine Res 2001;21:655-661.
Vidal V et al. Enhanced maturation and functional capacity of monocyte-derived immature dendritic cells by the synthetic immunomodulator Murabutide. Immunology 2001;103:479-487.
Vidal et al. Macrophage stimulation with Murabutide, an HIV-suppressive muramyl peptide derivative, selectively activates extracellular signal-regulated kinases 1 and 2, C/EBPbeta and STAT1: role of CD14 and Toll-like receptors 2 and 4. Eur J Immunol 2001;31:1962-1971.
Darcissac et al. The synthetic immunomodulator murabutide controls human immunodeficiency virus type 1 replication at multiple levels in macrophages and dendritic cells. J Virol 2000;74:7794-7802.
Darcissac et al. Selective potentiation of cytokine expression in human whole blood by murabutide, a muramyl dipeptide analogue. Cytokine 1996;8:658-666.
Bahr et al. Enhancement in vivo of the antiinflammatory and antitumor activities of type I interferon by association with the synthetic immunomodulator murabutide. J Interferon Cytokine Res 1996;16:297-306.

(Continued)

*Primary Examiner* — Janet L Andres
*Assistant Examiner* — Barry A Chestnut
(74) *Attorney, Agent, or Firm* — George A. Leone; Citadel Patent Law (57) ABSTRACT

A method for eliciting an immune response by contacting a mucosal surface utilizing a composition including an antigen, a NOD agonist, and a mucoadhesive, wherein the NOD agonist is N-Acetyl-muramyl-L-Alanyl-D-Glutamin-n-butyl-ester ("Murabutide").

20 Claims, 7 Drawing Sheets

(56) References Cited

OTHER PUBLICATIONS

Bahr et al. Synergistic effects between recombinant interleukin-2 and the synthetic immunomodulator murabutide: selective enhancement of cytokine release and potentiation of antitumor activity. J Interferon Cytokine Res 1996;16:169-178.

Bahr et al. Immunopharmacological activities and clinical development of muramyl peptides with particular emphasis on murabutide. Int J Immunopharmacol 1995;17:117-131.

Telzak et al. Clinical evaluation of the immunoadjuvant murabutide, a derivative of MDP, administered with a tetanus toxoid vaccine. J Infect Dis 1986;153:628-633.

Krueger et al. Muramyl peptides. Variation of somnogenic activity with structure. J Exp Med 1984;159:68-76.

Chedid et al. Biological activity of a new synthetic muramyl peptide adjuvant devoid of pyrogenicity. Infect Immun 1982;35:417-424.

McAdam et al. Amyloidosis and the serum amyloid A protein response to muramyl dipeptide analogs and different mycobacterial species. Infect Immun 1983;39:1147-1154.

Koga et al. Muramyl dipeptide induces acute joint inflammation in the mouse. Microbiol Immunol 1986;30:717-723.

Zidek. Differences in proinflammatory activity of several immunomodulatory derivatives of muramyl dipeptide (MDP) with special reference to the mechanism of the MDP effects. Agents Actions 1992;36:136-145.

Riveau et al. Dissociation between muramyl dipeptide-induced fever and changes in plasma metal levels. Am J Physiol 1986;250:C572-577.

Olberling et al. Enhancement of antibody response to a natural fragment of streptococcal M protein by Murabutide administered to healthy volunteers. Int J Immunol 1983; 7:398.

Bahr. Immune and Antiviral Effects of the Synthetic Immunomodulator Murabutide; Molecular Basis and Clinical Potential. In: Hackett CJ and Harn DA, ed. Vaccine Adjuvants: Immunlogical and Clinical Principles. Humana Press Inc., Totowa, NJ. 2006, pp. 193-218.

Waters et al. Muramyl dipeptide stimulation of particle clearance in several animal species. J Reticuloendothel Soc 1980;28:457-471.

International Search Report, Jan. 26, 2011.

Written Opinion of the International Searching Authority, Jan. 26, 2011.

International Preliminary Report on Patentability, Sep. 27, 2011.

Requirement for Restriction/Election, U.S. Appl. No. 13/255,427, Sep. 9, 2012.

Response to Requirement for Restriction/Election, U.S. Appl. No. 13/255,427, Sep. 24, 2012.

Non-Final Rejection, U.S. Appl. No. 13/255,427, Oct. 11, 2012.

Response to Non-Final Rejection, U.S. Appl. No. 13/255,427, Mar. 8, 2013.

Final Rejection, U.S. Appl. No. 13/255,427, Jul. 1, 2013.

Applicant Initiated Interview Summary, U.S. Appl. No. 13/255,427, Oct. 29, 2013.

\* cited by examiner

MUCOSAL IMMUNIZATION

CROSS-REFERENCE TO RELATED APPLICATIONS

This application is a divisional of and claims priority from co-pending U.S. application Ser. No. 13/255,427 to Herbst-Kralovetz et al. filed Nov. 17, 2011 and entitled "Mucosal Immunization," the disclosure of which is incorporated by reference; and further claims priority from PCT Application No PCT/US10/28820 to Herbst-Kralovetz et al. filed Mar. 26, 2010 the disclosure of which is also incorporated by reference and further claims priority of U.S. Provisional Application No. 61/164,281 to Herbst-Kralovetz et al. filed Mar. 27, 2009, the disclosure of which is also incorporated by reference.

BACKGROUND OF THE INVENTION

1. Field of the Invention

The present invention relates generally to vaccines. More particularly, it concerns compositions of antigens and adjuvants, and methods of their use. In specific embodiments, the invention concerns compositions comprising virus-like particle ("VLF") antigens and Murabutide.

2. Description of Related Art

Virus-like particles ("VLPs") typically consist of assembled protein subunits of a pathogenic virus that are capable of inducing an anti-viral (protective or therapeutic) immune response when administered to a subject, but are devoid of some or all of the nucleic acids necessary for viral replication. Thus, VLPs embody the best features of immunization with live or attenuated viruses, namely the induction of a relevant immune response, but lack the potential for causing disease because of the inability of the VLP to replicate in the subject.

There are many examples of VLPs and VLP-vaccine technology, and the use of VLPs as a vaccine platform finds particular value in mucosal immunization against viral pathogens. Examples of target diseases that can be treated by VLP immunization (prophylactically), or which might be ameliorated in terms of severity by VLP treatment after viral infection (therapeutically) include influenza ("flu") virus, hepatitis viruses, caliciviruses and essentially any virus whose capsid subunits can assemble into stable VLP after production.

While the immunogenicity and potential clinical benefit of VLPs have been demonstrated, as with any vaccine antigen, VLP immunogenicity might not always be sufficiently strong to mount a protective response—that is, an immune response might be induced by vaccination with a VLP antigen, but the strength, type and/or duration of the response might not be sufficiently robust to fend off disease upon a subject's exposure to the viral pathogen. Adjuvants are often used in conjunction with vaccine antigens to correct the inherent deficiencies of weak antigens. Adjuvants include molecules in many chemical and biological categories, with equally diverse modes of action. Modes of action of adjuvants include immunomodulation, antigen presentation enhancement, cytotoxic T-lymphocyte (CTL) induction, antigen targeting promotion, and depot generation. Examples of vaccine adjuvants include those that trap the antigen in a depot, such as alum, and enable immune system cells to sample and process the adjuvant over time, with an enhanced immune potentiating effect. Cytokines (cellular and immune regulatory molecules), such as granulocyte-macrophage colony stimulating factor (GM-CSF), have been used to cause a local inflammatory reaction to enhance exposure of immune cells to the antigen and to enhance the magnitude and duration of the immune response.

Presentation of a vaccine antigen, including VLP, through mucosal exposure (e.g. nasal, pulmonary, oral, vaginal) can lead to the development of mucosal immune protective effects, such that when a subject is exposed to a viral pathogen that gains entry through a mucosal surface the subject can be protected by this mode of vaccination. As summarized above, mucosal vaccination through exposure to an antigen by itself might not lead to protective immunity, and adjuvants can be used to overcome this deficiency. However, the field of mucosal vaccination is relatively new, unlike the more typical routes of intramuscular and subcutaneous vaccine administration, for which typical adjuvants include those that form a depot such as alum or enhance local inflammatory effects, such as cytokines. Consequently, there is a great need for new appropriate, safe and effective mucosal vaccine adjuvants. The present invention addresses this challenge with technology for adjuvanting (potentiating) the immune response to antigens, such as VLPs.

SUMMARY OF THE INVENTION

In one embodiment, the present invention provides a method of eliciting an immune response in a subject comprising contacting a mucosal surface of the subject with an antigen and an adjuvant selected from the group consisting of TLR agonists and NOD agonists, wherein an immune response to the antigen is elicited in the subject.

In another embodiment, the present invention provides a method of vaccinating a subject comprising contacting a mucosal surface of the subject with an antigen and an adjuvant selected from the group consisting of TLR agonists and NOD agonists, wherein a protective immune response to the antigen is elicited in the subject.

In certain aspects, the present invention provides a method of enhancing the immunogencity of an antigen in a subject comprising contacting a mucosal surface of the subject with the antigen and an adjuvant selected from the group consisting of TLR agonists and NOD agonists, wherein an immune response to the antigen is enhanced as compared to an immune response elicited by the antigen when administered without the adjuvant.

In another embodiment, the present invention provides a method of treating a viral disease, comprising administering to a mucosal surface of a subject a viral antigen and an adjuvant selected from the group consisting of endosomal TLR agonists and NOD agonists, wherein the viral disease is treated. In certain aspects, the disease is acute viral enteritis ("stomach flu"), and the viral antigen is a norovirus (including Norwalk virus) VLP.

In certain embodiments, the present invention provides a method of eliciting an immune response in a subject comprising contacting a mucosal surface of the subject with an antigen and a NOD agonist, wherein an immune response to the antigen is elicited in the subject. In certain aspects, the method further comprises contacting the mucosal surface of the subject with a TLR agonist.

In another embodiment, the present invention provides a method of vaccinating a subject comprising contacting a mucosal surface of the subject with an antigen and a NOD agonist, wherein a protective immune response to the antigen is elicited in the subject. In certain aspects, the method further comprises contacting the mucosal surface of the subject with a TLR agonist.

In certain aspects, the present invention provides a method of enhancing the immunogenicity of an antigen in a subject comprising contacting a mucosal surface of the subject with the antigen and a NOD agonist, wherein an immune response to the antigen is enhanced as compared to an immune response elicited by the antigen when administered without the NOD agonist. In certain aspects, the method further comprises contacting the mucosal surface of the subject with a TLR agonist.

In another embodiment, the present invention provides a method of treating a viral disease, comprising administering to a mucosal surface of a subject a viral antigen and a NOD agonist, wherein the viral disease is treated. In certain aspects, the disease is acute viral enteritis ("stomach flu"), and the viral antigen is a norovirus (including Norwalk virus) VLP. In certain aspects, the method further comprises contacting the mucosal surface of the subject with a TLR agonist.

The antigen may be any substance that prompts the generation of antibodies when administered to a subject. An antigen may be, for example, a protein or a polysaccharide. In certain embodiments, the antigen is from a pathogen. In some embodiments, the antigen is a bacterial antigen or a viral antigen. In some embodiments, the antigen is a virus-like particle (VLP). The VLP may be derived from any virus whose capsid subunits can assemble into a stable VLP. For example, the VLP may be a norovirus, calicivirus, hepatitis virus, papilloma virus, or influenza virus VLP.

In certain embodiments, the NOD agonist is a molecule that comprises a muramyl dipeptide (MDP) structure. The MDP may be naturally occurring or synthetic. In certain embodiments, the NOD agonist is Murabutide (N-Acetyl-muramyl-L-Alanyl-D-Glutamin-n-butyl-ester), which is a synthetic molecule derived from the MDP of a bacterial peptidoglycan. In certain embodiments, the NOD agonist is a NOD1 or a NOD2 agonist. The NOD agonist may be, for example, iE-DAP, Tri-DAP, C12-iE-DAP. M-TriDAP, L18-MDP, or peptidoglycans.

In some embodiments, the TLR agonist is an endosomal TLR agonist. In some embodiments, the TLR agonist is a PRR (pattern recognition receptor), CpG DNA, gardiquimod, or resiquimod. In one embodiment, a composition is formulated to contain 1 to 1,000 micrograms, 10 to 500 micrograms, or 10 to 250 micrograms of TLR agonist per dose. In certain aspects, the composition is formulated to contain about 10 micrograms of the TLR agonist per dose.

In certain aspects of the invention, the agonist is administered at the mucosal surface at a level of 1 to 1,000 micrograms per dose, 10 to 500 micrograms per dose, or 10 to 250 micrograms per dose.

The antigen and the adjuvant (NOD agonist and/or TLR agonist) may be combined in a single composition or they can be in separate compositions. When provided as separate compositions, the antigen and adjuvant may be administered at the same time or at different times. The composition may comprise a pharmaceutically acceptable carrier. In some embodiments, the carrier is a mucoadhesive. Mucoadhesives aid in retaining the antigen at or near the mucosa for a sufficient period of time to ensure adequate bioavailability of the antigen. The mucoadhesive may be a polymer, such as a polyethylene oxide homopolymer, poly vinyl pyrrolidone (PVP), methyl cellulose (MC), sodium carboxy methylcellulose (SCMC), hydroxy propyl cellulose (HPC), Carbopol, polyacrylate, chitosan, or polysaccharide. In one embodiment, the mucoadhesive is derived from Aloe vera polyshaccharides. The mucoadhesive polymer may be hydrophilic or a hydrogel.

The composition may be formulated as a gel, foam, suppository, film, tape, tablet, pastes, microparticle, syrup, spray, aerosol, or other form suitable for delivery to the mucosa.

In certain embodiments, the adjuvant is conjugated to or encapsulated within the VLP structure to form a VLP/adjuvant complex.

The term "treatment" refers to the administration or application of a remedy or remedies to a patient for a disease or an injury. The treatment need not effect the cure or prevention of a disease or injury, although a cure or prevention may be achieved in some patients receiving treatment. A treatment may be prophylactic in that it is administered before the patient has the disease or injury that is being treated, or treatment may be therapeutic in that it is administered to a patient who has the disease or injury.

In another embodiment, the present invention provides a composition comprising an antigen, an adjuvant selected from the group consisting of TLR agonists and NOD agonists, and a mucoadhesive. In certain aspects, the antigen is a viral antigen. In another embodiment, the present invention provides a composition comprising an antigen, a NOD agonist, and a mucoadhesive. In another embodiment, the present invention provides a composition comprising an antigen, a TLR agonist, a NOD agonist, and a mucoadhesive. In certain aspects, the antigen is a viral antigen. In certain aspects, the antigen is a viral antigen. In some embodiments, the viral antigen is a virus-like particle (VLP). In some embodiments, the NOD agonist is a muramyl dipeptide derivative, such as the muramyl dipeptide derivative N-Acetyl-muramyl-L-Alanyl-D-Glutamin-n-butyl-ester ("Murabutide"). In certain aspects, the composition is formulated with the adjuvant conjugated to or encapsulated within a VLP structure to form a VLP/adjuvant complex. In one embodiment, the composition is formulated to contain 1 to 1,000 micrograms, 10 to 500 micrograms, or 10 to 250 micrograms of adjuvant per dose. In certain aspects, the composition is formulated to contain about 25, 100, or 250 micrograms per dose. In some embodiments, the composition is formulate for delivery to the mucosa. The composition may be formulated as, for example, a gel, foam, suppository, film, tape, tablet, pastes, microparticle, syrup, spray, aerosol, or other form suitable for delivery to the mucosa.

Two or more NOD agonists, TLR agonists, or combinations thereof, may be combined in the above-mentioned methods and combinations.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, device, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, device, or system that "comprises," "has," "contains," or "includes" one or more recited features possesses those features, but is not limited to possessing only those features; it may possess features that are not recited. Furthermore, a structure or technique that is configured in a certain way must be configured in at least that way, but also may be configured in a way or ways that are not specified.

Any embodiment of any of the present methods, devices, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present invention provides methods and compositions that enhance immunization with a wide range of antigens, particularly immunizations delivered via mucous membranes. Many pathogens, including viruses, bacteria, and fungi, can enter the body through the mucous membranes. Accordingly, immunization by this route is an attractive option.

A type of viral antigen that may be used in the methods and compositions described herein are Virus-like particles ("VLPs"). VLPs consist of viral proteins derived from the structural proteins of a virus. They resemble the virus from which they are derived, but lack the viral nucleic acid. The lack of vial nucleic acid means that VLPs are not infectious. VLPs, therefore, are useful in vaccines, and several VLP-based vaccines have been approved by the U.S. Food and Drug Administration. Essentially any virus whose capsid subunits can assemble into a stable VLP can be used in a VLP-based vaccine. Examples of target diseases that can be treated by VLP immunization (prophylactically), or which might be ameliorated in terms of severity by VLP treatment after viral infection (therapeutically) include influenza ("flu") virus, hepatitis viruses, human papillomavirus, and caliciviruses.

While the immunogenicity and potential clinical benefit of VLPs have been demonstrated, as with any vaccine antigen, VLP immunogenicity might not always be sufficiently strong to mount a protective response—that is, an immune response might be induced by vaccination with a VLP antigen, but the strength, type and/or duration of the response might not be sufficiently robust to fend off disease upon a subject's exposure to the viral pathogen. Adjuvants are often used in conjunction with vaccine antigens to correct the inherent deficiencies of weak antigens. Adjuvants include molecules in many chemical and biological categories, with equally diverse modes of action. Modes of action of adjuvants include immunomodulation, antigen presentation enhancement, cytotoxic T-lymphocyte (CTL) induction, antigen targeting promotion, and depot generation. Examples of vaccine adjuvants include those that trap the antigen in a depot, such as alum, and enable immune system cells to sample and process the adjuvant over time, with an enhanced immune potentiating effect. Cytokines (cellular and immune regulatory molecules), such as granulocyte-macrophage colony stimulating factor (GM-CSF), have been used to cause a local inflammatory reaction to enhance exposure of immune cells to the antigen and to enhance the magnitude and duration of the immune response.

Figure 1:
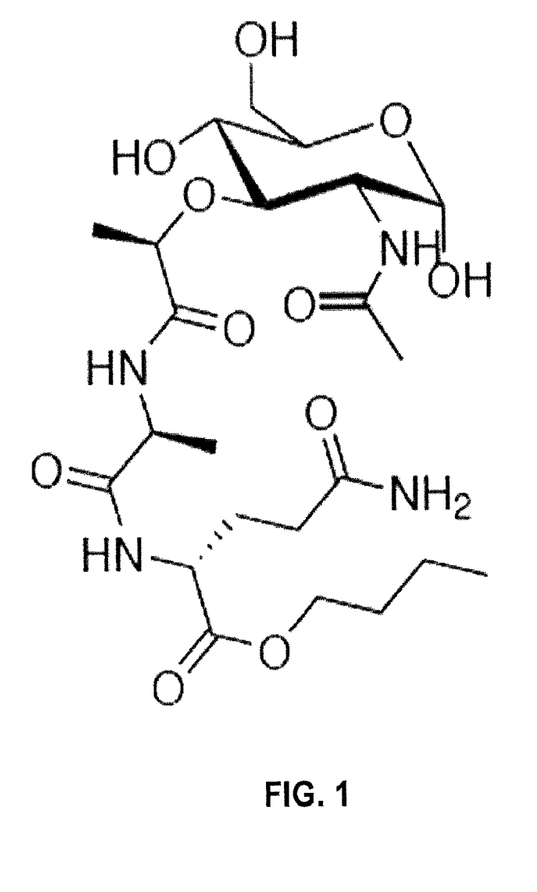
FIG. 1. Chemical structure of N-Acetyl-muramyl-L-Alanyl-D-Glutamin-n-butyl-ester ("Murabutide").

It was shown that when a model VLP, namely, norovirus capsid protein ("NVCP") VLP, was administered to experimental animals through the nasal mucosa by itself, relatively poor antigen-relevant immune responses were measured. However, when NVCP was administered with various known adjuvants, including alum, cholera toxin subunit (CT), CpG DNA, gardiquimod or resiquimod, much more robust immune responses resulted. These adjuvants have been studied by others with respect to their utility in mucosal immunization. In studying additional adjuvants known to be active through conventional parenteral administration (i.e. subcutaneous; intramuscular; etc.), an unexpectedly beneficial response resulted from a synthetic derivative of muramyl dipeptide—Murabutide (N-Acetyl-muramyl-LA-lanyl-D-Glutamin-n-butyl-ester) (FIG. 1). Murabutide is a NOD2 agonist. NOD receptors have not been as well characterized as TLR receptors in the mucosa. Accordingly, the distribution and expression levels of NOD receptors in mucosa, such as nasal mucosa, was not well known. The beneficial response achieved with Murabutide when administered to the mucosa was, therefore, surprising. NVCP is a model antigen for mucosal immunization as well as a candidate vaccine VLP for managing norovirus (including Norwalk virus) infections, which cause severe gastrointestinal pathology (acute viral enteritis; "stomach flu").

Murabutide, when used in conjunction with a VLP antigen, such as NVCP, and both are applied to a mucosal surface, such as a nasal, buccal, oral, intestinal, ocular, pulmonary, vaginal, genital, or other mucosal tissue or surface, strongly potentiates the magnitude and/or duration of an immune response. Accordingly, Murabutide as an adjuvant enhances immunization through a mucosal route of exposure, such that the subject develops an enhanced immune response to the antigen relative that the response obtained by exposing the subject to the antigen in the absence of the Murabutide adjuvant. This permits the enhanced immunization of a subject for prophylaxis or therapeutic protection against a pathogenic virus, by administering to a subject a VLP antigen in conjunction with Murabutide as an adjuvant through a mucosal route of exposure, such that the subject develops an enhanced immune response to the antigen relative that the response obtained by exposing the subject to the antigen in the absence of the Murabutide adjuvant. The formulation of said antigen, in particular a VLP antigen, and the Murabutide adjuvant, and the administration of the antigen, including a VLP antigen, and the Murabutide adjuvant, includes methods and compositions well known to those skilled in the art of vaccine development and are selected on the basis of safety, efficacy, ease of administration to a subject, cost and other considerations depending on the indication for which the vaccine and adjuvant are intended.

The methods and compositions describe herein employ adjuvants to enhance immunization with a wide range of antigens. In certain embodiments, the adjuvant is a muramyl dipeptide or a derivative of a muramyl dipeptide. For example, Murabutide (N-Acetyl-muramyl-LAlanyl-D-Glutamin-n-butyl-ester; $C_{23}H_{40}N_4O_{11}$; MW=548.58) is a synthetic immunomodulator derived from muramyl dipeptide. Murabutide, however, is devoid of the pyrogenic and somnogenic activities of muramyl dipeptide. Murabutide is a NOD2 ligand. Murabutide, when used in conjunction with a VLP antigen, such as NVCP, and both are applied to a mucosal surface, such as a nasal, buccal, oral, intestinal, ocular, pulmonary, vaginal, genital, or other mucosal tissue or surface, can strongly potentiate the magnitude and/or duration of an immune response.

The mucous membranes are linings of mostly endodermal origin, covered in epithelium. They line various body cavities and organs that are exposed to the external environment, including much of the pulmonary and digestive systems. Some examples of mucous membranes include: buccal mucosa, esophageal mucosa, gastric mucosa, intestinal mucosa, nasal mucosa, olfactory mucosa, oral mucosa, bronchial mucosa, uterine mucosa, and endometrium. The compositions disclosed herein may be formulated for delivery to mucous membranes.

The compositions will generally be prepared as essentially free of impurities that could be harmful to humans or animals. The preparation of a pharmaceutical composition including an antigen and an adjuvant will be known to those of skill in the art in light of the present disclosure, as exemplified by Remington's Pharmaceutical Sciences, 18th Ed. Mack Printing Company, 1990, incorporated by reference. Moreover, for animal (e.g., human) administration, it will be understood that pharmaceutical preparations should meet sterility, pyrogenicity, general safety and purity standards. Aqueous compositions of an antigen and adjuvant comprise effective amounts of the antigen and the adjuvant dispersed in a pharmaceutically or pharmacologically acceptable carrier.

The phrases "pharmaceutically acceptable" and "pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, and such like materials and combinations thereof, as would be known to one of ordinary skill in the art (see Remington's, 1990). The use of such carriers for pharmaceutically active substances is well know in the art. Except insofar as any conventional carrier is incompatible with the antigens and adjuvants of in the composition, its use in therapeutic compositions is contemplated. Supplementary active ingredients also can be incorporated into the compositions.

Under ordinary conditions of storage and use, pharmaceutical preparations may further contain a preservative to prevent growth of microorganisms. Preservatives include antimicrobial agents, antioxidants, chelating agents and inert gases. The pH and exact concentration of the various components in the pharmaceutical are adjusted according to well-known parameters.

An effective amount of a therapeutic composition is determined based on the intended goal. "Effective amounts" are those amounts effective to produce beneficial results in the recipient animal or patient. Such amounts may be initially determined by studies in experimental animals. Preferred animal models for use in certain embodiments are rodent models (e.g., mouse and rat), which are preferred because they are economical to use and, particularly, because the results gained are widely accepted as predictive of clinical value. The term "unit dose" refers to a physically discrete unit suitable for use in a subject, each unit containing a predetermined quantity of the composition calculated to produce the desired response in association with its administration, i.e., the appropriate route and treatment regimen. The quantity to be administered, both according to number of treatments and unit dose, depends on the subject to be treated, the state of the subject, the disease being treated, and the protection desired. Precise amounts of the therapeutic composition also depend on the judgment of the practitioner. The actual dosage amount of a composition of the present invention administered to a patient can be determined by physical and physiological factors such as age, body weight, severity of condition, the type of disease being treated, previous or concurrent therapeutic interventions, idiopathy of the patient and on the route of administration.

The composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compositions of the present invention may comprise different types of carriers depending on whether it is to be administered in solid, gel, liquid, or aerosol form, and whether it needs to be sterile for such routes of administration.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof. As discussed above, mucoadhesives are particularly suitable as carriers when the route of administration is via the mucosa.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions may be prepared so that they are similar in many respects to nasal secretions, so that normal ciliary action is maintained. Thus, in certain embodiments, the aqueous nasal solutions are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation.

In certain embodiments, the compositions are prepared for administration by such routes as oral ingestion. In these embodiments, the composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, films, or combinations thereof. Carriers for oral administration may comprise inert diluents, assimilable edible carriers or combinations thereof. In other aspects of the invention, the oral composition may be prepared as a syrup or elixir. A syrup or elixir may comprise, for example, at least one active agent, a sweetening agent, a preservative, a flavoring agent, a dye, a preservative, or combinations thereof.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

The following examples are included to demonstrate certain embodiments of the invention. Those of skill in the art should, in light of the present disclosure, appreciate that many changes can be made in the specific embodiments that are disclosed and still obtain a like or similar result without departing from the spirit and scope of the invention.

Figure 2:
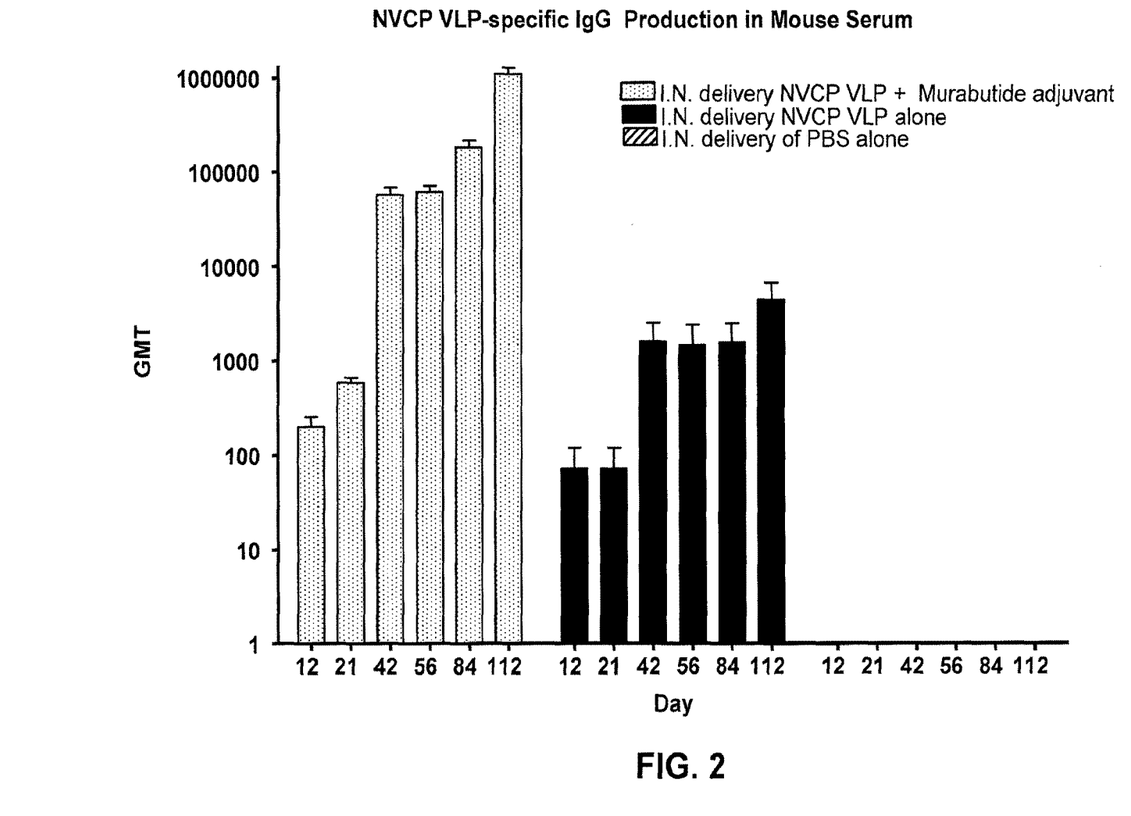
FIG. 2. NVCP VLP-specific IgG production in mouse serum.
Figure 3:
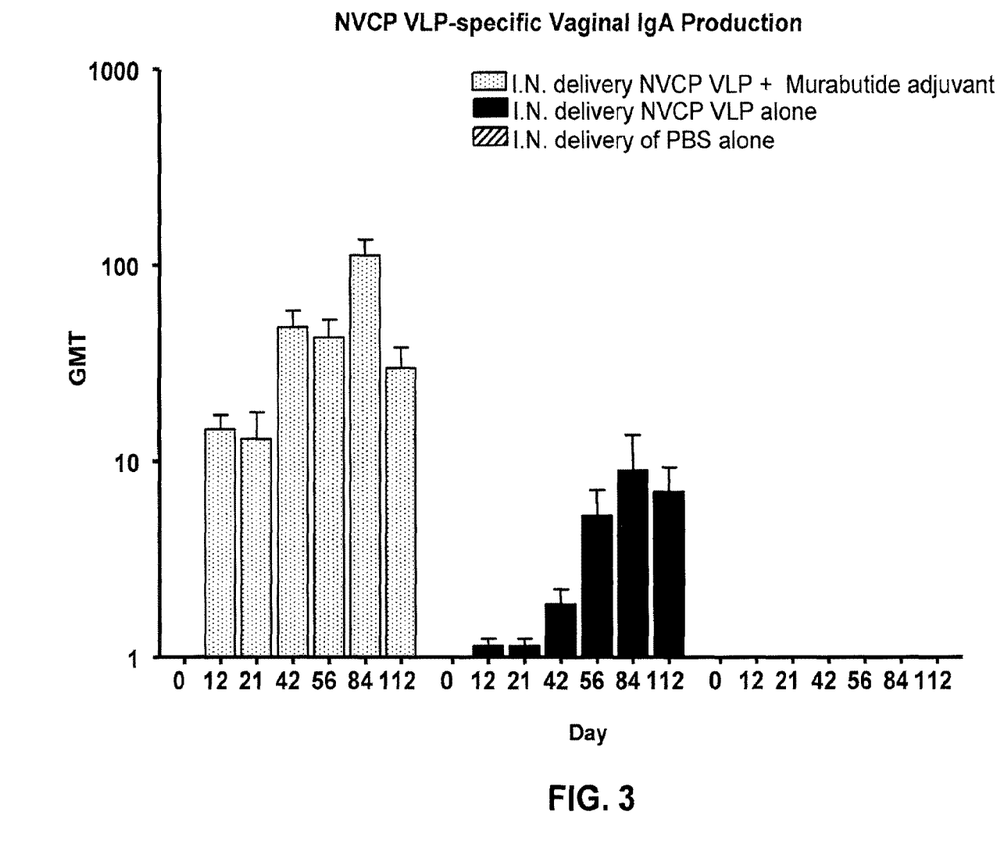
FIG. 3. NVCP VLP-specific vaginal IgA production.
Figure 4:
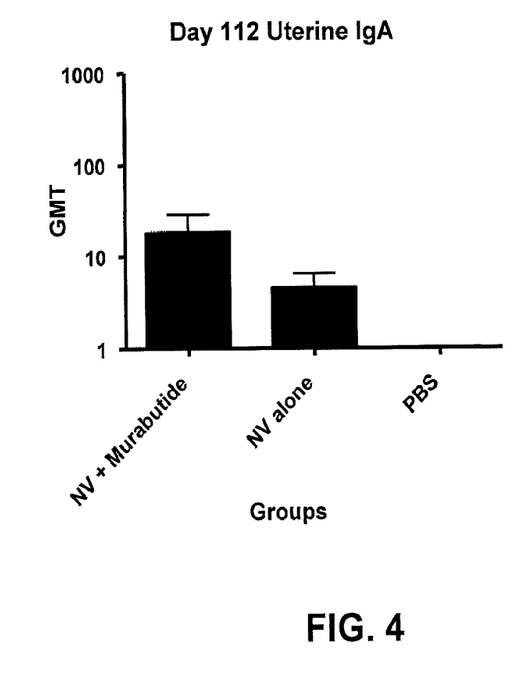
FIG. 4. NVCP VLP-specific uterine IgA production.
Figure 5:
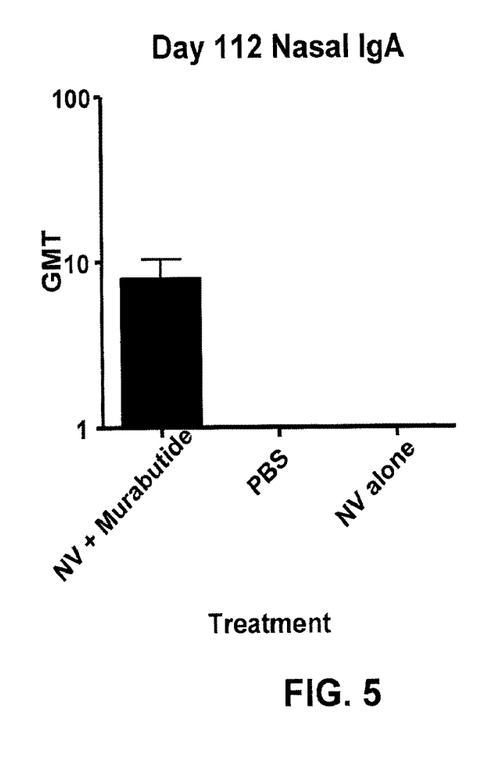
FIG. 5. NVCP VLP-specific nasal IgA production.
Figure 6:
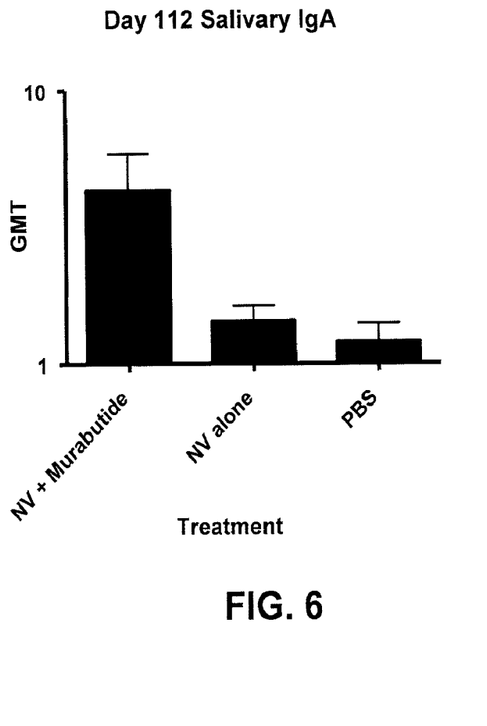
FIG. 6. NVCP VLP-specific salivary IgA production.

Norovirus capsid protein ("NVCP") VLP was administered to mice through the nasal mucosa alone or in combination with Murabutide. NVCP VLP-specific antibody titers were evaluated at various points following the administration of the antigen. As shown in FIG. 2, intranasal administration of NVCP VLP in combination with Murabutide greatly increased the level of NVCP VLP-specific IgG antibodies in serum when compared to intranasal administration of NVCP VLP alone. FIG. 3 shows that NVCP VLP-specific vaginal IgA production also was greatly increased in the group receiving intranasal administration of NVCP VLP combination with Murabutide as compared to the group receiving NVCP VLP alone. Similar results were observed when IgA titers were evaluated at 112 days in uterine mucosa, nasal mucosa, and salivary mucosa, as shown in FIGS. 4, 5, and 6.

Figure 7:
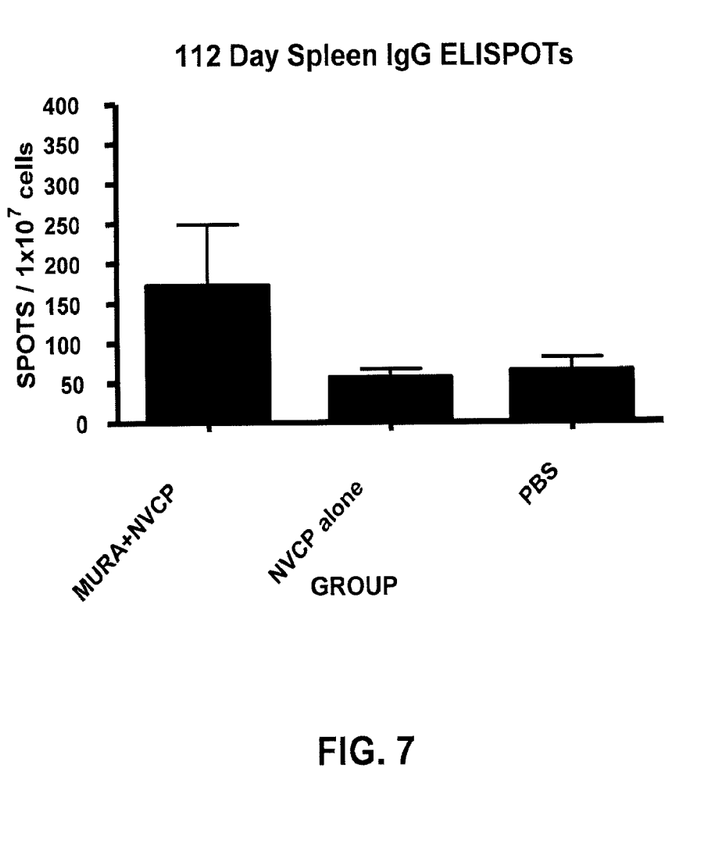
FIG. 7. NVCP VLP-specific spleen IgG ELISPOTs.

As shown in FIG. 7, intranasal administration of NVCP VLP in combination with Murabutide greatly increased the level of NVCP VLP-specific IgG antibodies, as determined by ELISPOT, in mouse spleen when compared to intranasal administration of NVCP VLP alone.

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for eliciting an immune response comprising:
   making a composition formulated for delivery to mucous membranes where the composition consists essentially of an antigen, a NOD agonist, and a mucoadhesive, wherein the NOD agonist is N-Acetyl-muramyl-L-Alanyl-D-Glutamin-n-butyl-ester (Murabutide); and
   administering the composition to a mucosal surface of a subject to elicit the immune response.

2. The method of claim 1, wherein the antigen is a virus-like particle (VLP).

3. The method of claim 1, wherein the VLP is derived from a norovirus, calicivirus, hepatitis virus, papilloma virus, or influenza virus.

4. The method of claim 1, wherein the antigen and the NOD agonist are combined in a single composition.

5. The method of claim 1, wherein the antigen and the NOD agonist are in separate compositions.

6. The method of claim 4, wherein the composition comprises a carrier.

7. The method of claim 6, wherein the carrier is a mucoadhesive.

8. The method of claim 6, wherein the mucoadhesive is derived from Aloe vera polysaccharides that are essentially free from impurities.

9. The method of claim 1, further comprising contacting the mucosal surface of the subject with a TLR agonist.

10. The method of claim 9, wherein the TLR agonist is a pattern recognition receptor (PRR).

11. A method of treating a viral disease, comprising administering to a mucosal surface of a subject a viral antigen and a NOD agonist, wherein the viral disease is treated.

12. The method of claim 11, wherein the viral disease is treated prophylactically.

13. The method of claim 11, wherein the viral disease is treated therapeutically.

14. The method of claim 11, wherein the antigen is a virus-like particle (VLP).

15. The method of claim 14, where the VLP is derived from a calicivirus, hepatitis virus, or influenza virus.

16. The method of claim 11, further comprising administering to the mucosal surface of the subject a TLR agonist.

17. The method of claim 16, wherein the TLR agonist is a CpG DNA, gardiquimod, or resiquimod.

18. The method of claim 1, wherein the murabutide is administered at the mucosal surface at a level of 1 to 1,000 micrograms per dose.

19. The method of claim 18, wherein the murabutide is administered at the mucosal surface at a level of 10 to 500 micrograms per dose.

20. The method of claim 19, wherein the murabutide is administered at the mucosal surface at a level of 10 to 250 micrograms per dose.

* * * * *